United States Patent
Nebl et al.

(10) Patent No.: US 11,826,943 B2
(45) Date of Patent: Nov. 28, 2023

(54) MACHINE AND METHOD FOR TREATING AND IN PARTICULAR TRANSPORTING PLASTIC PARISONS

(71) Applicant: KRONES AG, Neutraubling (DE)

(72) Inventors: Florian Nebl, Mintraching (DE); Dieter Wuensche, Straubing (DE); Juergen Soellner, Beratzhausen (DE)

(73) Assignee: KRONES AG

( * ) Notice: Subject to any disclaimer, the term of this patent is extended or adjusted under 35 U.S.C. 154(b) by 651 days.

(21) Appl. No.: 16/620,244

(22) PCT Filed: Jun. 5, 2018

(86) PCT No.: PCT/EP2018/064704
§ 371 (c)(1),
(2) Date: Dec. 6, 2019

(87) PCT Pub. No.: WO2018/224472
PCT Pub. Date: Dec. 13, 2018

(65) Prior Publication Data
US 2020/0180204 A1    Jun. 11, 2020

(30) Foreign Application Priority Data
Jun. 6, 2017 (DE) .................... 10 2017 112 455.1

(51) Int. Cl.
*B29C 49/42* (2006.01)
*B29C 49/06* (2006.01)
(Continued)

(52) U.S. Cl.
CPC .......... *B29C 49/06* (2013.01); *B29C 49/4205* (2013.01); *A61L 2202/23* (2013.01);
(Continued)

(58) Field of Classification Search
CPC .................... B29C 49/4205; B29C 2049/4697
See application file for complete search history.

(56) References Cited

U.S. PATENT DOCUMENTS

| 4,268,975 A | 5/1981 | Schall et al. ..................... 34/105 |
| 5,326,258 A | 7/1994 | Gittner et al. ..................... 432/5 |

(Continued)

FOREIGN PATENT DOCUMENTS

| DE | 20308513 U1 * | 8/2004 | ......... B29C 49/4205 |
| DE | 102009016593 | 10/2010 | ............. B29C 49/42 |

(Continued)

OTHER PUBLICATIONS

International Search Report and Written Opinion (w/translations) issued in application No. PCT/EP2018/064704, dated Sep. 21, 2018 (18 pgs).

(Continued)

*Primary Examiner* — Robert B Davis
(74) *Attorney, Agent, or Firm* — HAYES SOLOWAY P.C.

(57) ABSTRACT

Disclosed is a device for handling plastic parisons with a storage device which serves for storing a plurality of plastic parisons and with at least one transport device which transports the plastic parisons along a predetermined transport path from the storage device to a processing device. At least one portion of the storage device and/or of the transport path is enclosed by a housing device and an application device is provided which applies a flowable and in particular gaseous medium to an interior of this housing device.

11 Claims, 3 Drawing Sheets

(51) Int. Cl.
*B29C 49/46* (2006.01)
*B29L 31/00* (2006.01)

(52) U.S. Cl.
CPC ...... *B29C 49/46* (2013.01); *B29C 2049/4679* (2013.01); *B29C 2049/4697* (2013.01); *B29L 2031/7158* (2013.01)

(56) References Cited

U.S. PATENT DOCUMENTS

| | | | |
|---|---|---|---|
| 2007/0108018 A1 | 5/2007 | Charpentier | 198/434 |
| 2009/0155036 A1 | 6/2009 | Deyerl | 414/539 |
| 2009/0230124 A1 | 9/2009 | Senn | 219/679 |
| 2011/0061343 A1 | 3/2011 | Roithmeier et al. | 53/452 |
| 2011/0198270 A1 | 8/2011 | Beutl et al. | 209/552 |
| 2011/0291332 A1 | 12/2011 | Voth et al. | 264/532 |
| 2013/0061557 A1 | 3/2013 | Kitano et al. | 53/167 |
| 2014/0260099 A1* | 9/2014 | Braum | B29C 49/46 53/510 |
| 2014/0318083 A1 | 10/2014 | Marastoni | B65B 3/022 |
| 2014/0322074 A1 | 10/2014 | Seidenberg | A61L 2/16 |
| 2015/0151478 A1 | 6/2015 | Heller et al. | B29C 49/4205 |
| 2015/0225098 A1 | 8/2015 | Söllner et al. | B65B 31/025 |
| 2015/0258727 A1 | 9/2015 | Heller et al. | B29C 49/4205 |
| 2016/0368197 A1 | 12/2016 | Takahashi et al. | B29C 49/68 |

FOREIGN PATENT DOCUMENTS

| | | | |
|---|---|---|---|
| DE | 102012107961 | 5/2014 | B29C 49/69 |
| DE | 102012217457 | 5/2014 | B29C 49/46 |
| EP | 2711158 | 3/2014 | B29C 49/36 |
| FR | 2556273 | 6/1985 | B29C 49/02 |
| JP | H11291331 | 10/1999 | B29C 49/06 |
| JP | 2016193622 | 11/2016 | B29C 49/42 |
| WO | 2012126129 | 9/2012 | B65G 65/23 |
| WO | 2015193351 | 12/2015 | B29C 49/42 |

OTHER PUBLICATIONS

German Search Report (w/machine translation) issued in application No. 10 2017 112 455.1, dated Mar. 26, 2018 (12 pgs).

Notice of Opposition filed in EPO Appln. Serial No. 18729111.7, dated Nov. 22, 2022, 19 pages.

* cited by examiner

MACHINE AND METHOD FOR TREATING AND IN PARTICULAR TRANSPORTING PLASTIC PARISONS

BACKGROUND OF THE INVENTION

The present invention relates to a machine and a method for treating plastic parisons and in particular for transporting plastic parisons. Such machines and methods have been known for a long lime from the prior art. In this case it is in particular known that starting from a store, such as for instance a preform chute or the like, plastic parisons are transported by means of various transport means to a blow moulding machine or an oven.

In the current state of the art the plastic parisons are transported during feeding by means of a silo, by means of feeder belts and a roller sorter. These said transport and sorting elements can be sealed off by simple covers against coarse dirt from the environment. The same also applies to an inclined feed rail often present between a roller sorter and a blow moulding machine in the prior art. In the design known from the prior art there is a substantial increase in contamination in this handling region of the plastic parisons between the removal of the plastic parisons from a container and a blow moulding machine. These contaminants must be eliminated again or the parisons must be sterilised in the subsequent processing at comparatively great expense.

Therefore, the object of the present invention is to minimise contamination of the plastic parisons on the way to a blow moulding machine and/or to reduce the sterilisation costs.

SUMMARY OF THE INVENTION

A device according to the invention for treating plastic parisons and in particular for transporting plastic parisons has a storage device which serves for storing a plurality of plastic parisons, as well as at least one transport device which transports the plastic parisons along a predetermined transport path from the storage device to a treatment device. Preferably at least two, preferably at least three transport devices are provided which transport the plastic parisons.

According to the invention at least one portion of the storage device and/or of the transport path is housed in a housing device and an application device is provided which applies a flowable and in particular gaseous medium to an interior of this housing device.

In other words at least a portion of the transport device is preferably also housed. The storage device can preferably be a silo, or a container, in which a plurality of plastic parisons can be accommodated.

An enclosure is understood below to mean at least surrounding the transport path in the peripheral direction thereof, hut optionally also a complete enclosure, that is to say a substantially closed-off space. Preferably, however, this enclosure can also have openings in order for example to carry out ventilation and extraction and/or in order to achieve a certain flow of the gaseous medium inside the housing or the enclosure. In particular an air stream is generated by means of these openings.

In a preferred method the processing device is selected from a group of processing devices which includes devices for reshaping plastic parisons into plastic containers, in particular blow moulding machines, sterilising devices for sterilising plastic parisons, ovens for heating plastic parisons and the like. In particular the processing machine is an oven which is suitable and intended for heating plastic parisons.

In a further advantageous embodiment the entire storage device and/or the entire transport path is enclosed by one or more housing devices. Both the entire storage device and also the entire transport path are preferably enclosed by a housing device. In this case these several housing devices can be connected to one another in such a way that the plastic parisons can be transported from one housing device into a further housing device. Adjacent housing devices can also have walls in common with one another.

In this way a controlled ventilation of the preform feed is provided, which covers the entire handling region of the plastic parisons, for example a tipper, a silo, feeder belts and also roller sorters including feed rails. In this case this region is preferably supplied with controlled clean and filtered air. In this way it is possible, in a substantially closed environment, to ensure a change of air for example 50 to 100 times per hour. Due to this change of air and the resulting slight positive pressure inside the enclosures, air which is polluted and/or contaminated with germs is preferably prevented from penetrating into the covered regions and so unnecessary contamination of the plastic parisons is prevented.

However, it is pointed out that this procedure does not enable sterilisation or holding in a clean room but as mentioned above, it enables the application of relatively clean or filtered air to the transport regions of the plastic parisons. However, a possibility is created for reducing the outlay for subsequent sterilisation. In this case the enclosures or housing also have openings which facilitate a vent stream in the interior of the enclosures. In this way the regions in which the plastic parisons are transported can always be supplied with fresh and/or filtered air.

Preferably at least one of the aforementioned housings is designed to be stationary. Particularly preferably a plurality of the housings are designed to be stationary and particularly preferably all of the aforementioned housings are designed to be stationary. In this case the housing can also have openings such as, in particular but not exclusively, inspection openings, which facilitate access to the individual machines as for instance the sorting device, for instance for repair and/or maintenance purposes.

In this way a contamination and/or pollution of the plastic parisons in the plastic parison feed lines is achieved. Thus this leads to a reduction of costs of sterilisation in follow-up processes or for increasing the effectiveness thereof when costs remain the same. Furthermore, a correspondingly well designed ventilation concept makes it possible to install the plastic parison food in front of any necessary clean rooms or also to create an option in which clean rooms can be omitted completely.

In a further advantageous embodiment the machine has, along the transport path of the plastic parisons, a sorting device and/or orienting device which is suitable and intended for sorting and/or orienting the plastic parisons. Different sorting devices, such as for example disc sorters or roller sorters, are known from the prior art Particularly preferably the sorting device in turn has two rotatable rollers which are spaced apart from one another and between which the plastic parisons can be transported.

Thus a so-called roller sorter is preferably proposed. In this case these two rotatable rollers are preferably spaced apart in such a way that a main body of the plastic parisons can pass through a gap formed between the rollers, but a carrying ring of the plastic parisons Is supported by the rollers. With a corresponding rotation of the rollers sorting of the plastic parisons is then possible.

These transport rollers are preferably slightly inclined, so that the plastic parisons are also transported when the rollers rotate in a specific transport direction. These sorting devices can be adjoined by further transport devices which transport the plastic parisons, already in a predetermined orientation, for example with their carrying rings or mouths upwards.

In a further advantageous embodiment the transport device as a whole also has at least one so-called inclined conveyor, which conveys the plastic parisons not in a horizontal direction or not only in a horizontal direction, but also in a vertical direction, in particular in order to bridge differences in height. In particular this inclined conveyor is suitable and intended for conveying the plastic parisons upwards.

In a further preferred embodiment the machine also has discharge rails. In addition the machine can also have at least one inspection device which is suitable and intended for inspecting specific regions of the plastic parisons, such as for instance mouth regions or also regions of the main body thereof. Advantageously in this case the transport paths of the plastic parisons are also enclosed by this inspection device and/or acted upon by filtered air and/or sterile air.

In a further advantageous embodiment the machine has a fitter device for filtering the gaseous medium to be fed to the interior of the housing device. In particular this filter device is suitable and Intended for filtering out germs from the air.

The application device preferably has a ventilator device for generating an air stream and in particular an air stream inside the housing. Advantageously this air stream also extends at least intermittently in the transport direction of the plastic parisons or counter to this transport direction.

This ventilator device advantageously has at least two ventilator units. In a further advantageous embodiment at least one ventilator device has an output which is between 1,000 and 3,500 m$^3$/h, preferably between 1,200 and 3,000 m$^3$/h and particularly preferably between 1,400 and 2,600 m$^3$/h. The output of the ventilators and/or the said volumes are generally dependent upon the layout of the system. It would also be conceivable that only one ventilator device is provided.

In a further advantageous embodiment at least one ventilator device is arranged inside a housing device which at least partially surrounds the storage device. Thus it is possible, for example, that the ventilator devices are accommodated in a silo enclosure or a tipper enclosure or in the enclosure of the storage device. Thus it is possible, for example, that the ventilator device is mounted directly above or over a silo, or also laterally, for example on the wall of the enclosure of the storage device, in addition it would also be conceivable that the ventilator device is arranged outside the housing.

In a preferred embodiment a housing which surrounds the storage device has an opening by means of which plastic parisons can be fed. In this case it is possible for example that containers with plastic parisons are introduced into the housing for example by means of a pallet conveyor or fork lift truck. The opening itself may be closeable for example by a roller shutter or sliding door.

In a further advantageous embodiment the application device has a supply line which is suitable and intended for bringing a gas stream generated by a ventilator device to a plurality of positions along the transport path of the plastic parisons. In this case it is pointed out that in some instances the transport path of the plastic parisons extends over large distances, in this way a supply line system is proposed, which is suitable and intended for generating a gas stream in a plurality of regions of the machine and in particular also at a plurality of regions along the transport path of the plastic parisons.

In a further advantageous embodiment this supply line has a main line which preferably has one or more branch lines or which feeds into one of these branch lines. In this case these branch lines can be led to individual housing parts. Thus individual housing parts can be supplied with air in each case.

In this case it would be possible that the machine has a complete housing which surrounds the entire transport path. However, it would also be possible that a plurality of housings are provided which are suitable and intended for surrounding a transport path of the plastic parsons like a channel, in this way the volume to which the air stream is applied can be kept relatively low.

In a further advantageous embodiment these supply lines have locking devices which are suitable and intended for throttling the air stream. Thus it is possible that the air stream is routed via a large supply line and via smaller branch lines into an introduction region of the individual transporters. In this case these branch lines are equipped with gate valves in order to control and in particular to throttle the air stream partially in individual regions of the transport path.

Thus it is possible for example that the air stream is routed via small supply lines into an introduction region of a roller sorter, a return belt and preferably also in a start region of discharge rails. The air preferably flows with the conveying direction to the respective transport end and escapes there. For this purpose the individual housing parts can in each case provide outlet openings which make it possible to create a targeted air stream.

As mentioned, these supply lines can preferably be shut off or the air stream flowing through these supply lines and in particular the above-mentioned branch lines can be regulated and in particular can be throttled. Thus it is possible that the above-mentioned branch lines are equipped with gate valves in order to control or to throttle the air stream. Thus it is possible to control and/or to regulate the air flows individually inside the individual devices. It is also conceivable and preferable that the output of the at least one ventilator device and generally the outputs of the plurality of ventilator devices can be regulated.

It is also possible for example that a roller sorter is adjoined by a further transport device such as a feed rail.

In a further advantageous embodiment the machine has a heating device which is suitable and intended for heating the plastic parisons. This heating device is preferably arranged in a transport direction of the plastic parisons after at least a part of the above-mentioned transport devices. Preferably no device is provided between the storage device and the aforementioned heating device for sterilising plastic parisons. In the prior art it is conventional in some instances to provide a sterilising device which is suitable and intended for sterilising plastic parisons in the region of the transport path from the storage device and the heating device. Due to the configuration of the machine according to the invention it is possible to dispense with such a sterilising device.

Furthermore, the present invention is directed to a method for treating plastic parisons, wherein a plurality of plastic parisons are stored in a storage device and these plastic parisons are transported by at least one transport device along a predetermined transport path from the storage device to a processing device.

According to the invention at least one portion of the storage device and/or of the transport path of the plastic parisons and for at least one transport device is enclosed by a housing device and an application device applies a flowable and in particular gaseous medium to an interior of this housing device. Particularly preferably this gaseous medium is air and in to particular filtered air.

In a further preferred method a positive pressure of the gaseous medium is generated in the interior of the housing device at least in some portions and/or at least intermittently. A laminar flow is preferably used. Particularly preferably this involves a slight positive pressure, which is preferably less than 20%, preferably less then 10% relative to the external pressure. In this way the air is drawn off again from individual housing parts via openings, so that an air stream of filtered or clean air prevails in the interior of the housing parts.

Therefore the gaseous medium is preferably filtered. In a further preferred method HEPA filters are used for filtering the gaseous medium.

BRIEF DESCRIPTION OF THE DRAWINGS

Further advantages and embodiments are apparent from the appended drawings in the drawings.

DETAILED DESCRIPTION OF THE INVENTION

Figure 1:
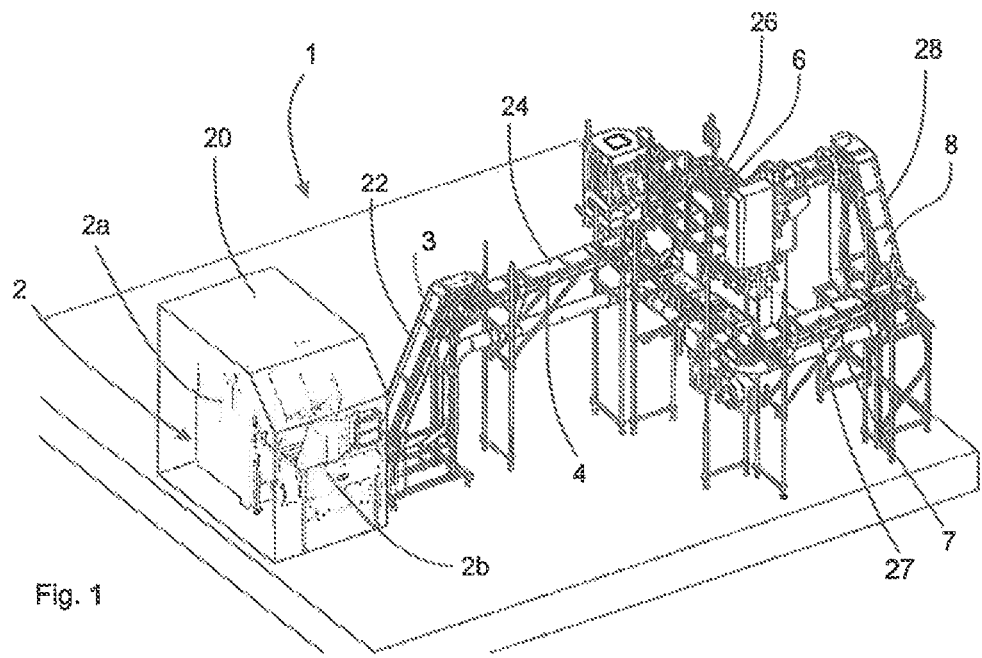
FIG. 1 shows an overall representation of a device 1 according to the invention.

FIG. 1 shows an overall representation of a device according to the invention. Here the housing 20 of the storage device 2, in this case more precisely a tipper 2a and a silo 2b, is shown as well as the housing 22, 24, 25, 26, 27 and 28 of the transport devices 3, 4, 5, 6, 7 and 8. The housing device 24 here surrounds a conveyor belt 4. The housing device 22 surrounds an inclined conveyor, which conveys the plastic parisons upwards and specifically in the direction of the said conveyor belt 4. The housing device 26 here surrounds a roller sorter 6. In this case the roller sorter 6 not only sorts the parisons, but also transports them.

In addition, housing devices 25 and 28 are also provided which surround the transport devices 5 and 8, wherein the transport device 8 is an intermediate silo.

Figure 2:
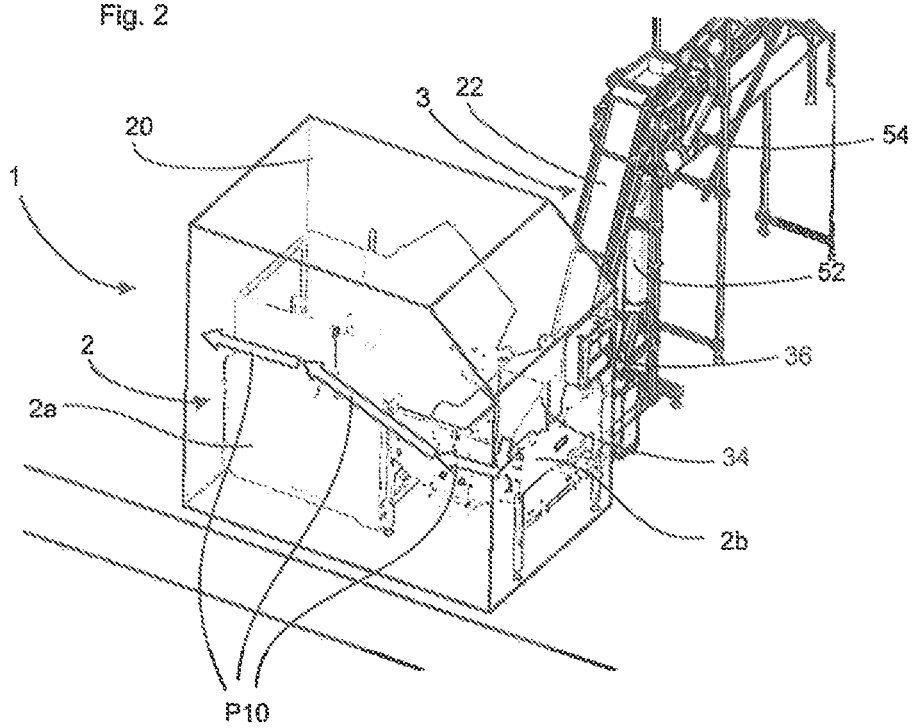
FIG. 2 shows a detail of the device shown in FIG. 1.

FIG. 2 shows a partial view of a device 1 according to the invention for treating and in particular transporting plastic parisons. In this case the reference 2 relates to a storage device in which a plurality of plastic parisons (not shown) are stored. In this case this storage device can for instance have a tipper 2a and a silo 2b. These plastic parisons enter the silo 2b and can be transported from there by means of a transport device 3 which is designed here as an inclined conveyor. The reference 20 designates an enclosure or a housing which completely surrounds the storage device 2, that is to say in this case in particular the tipper 2a and the silo 2b. The reference 34 designates a ventilator device which generates an air stream (arrow P10) inside the housing 20. In order to generate a directional air stream, the housing preferably has an opening to the rear through which the air stream can exit. The reference 36 designates a filter unit, by means of which ambient air is drawn in and in this way is also filtered.

Figure 3:
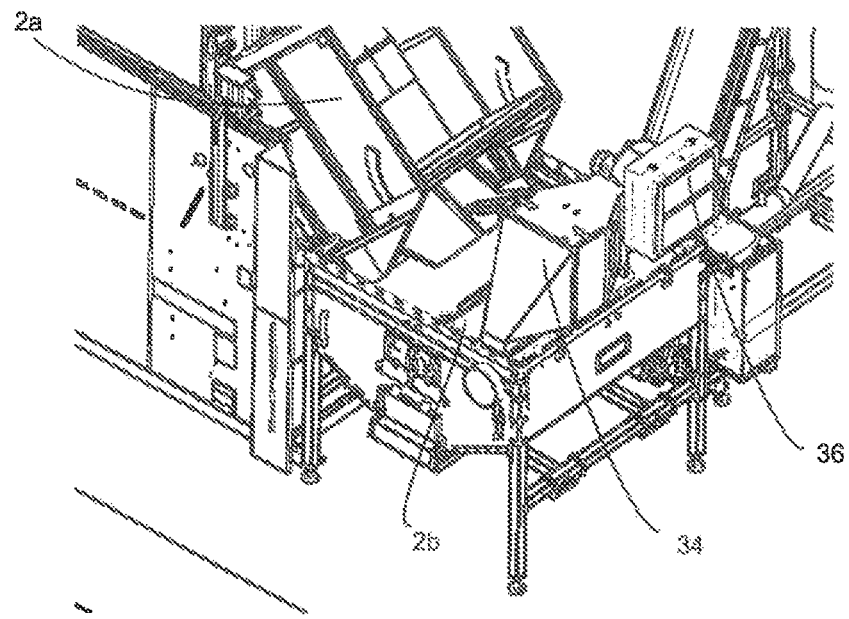
FIG. 3 shows a representation of the storage device of a device according to the invention.

FIG. 3 shows a detail of the device shown in FIG. 1. Here again the ventilator unit 34 is illustrated, and also the filter device 36 which is suitable for drawing in air. The reference 2a designates a tipper which serves for feeding the plastic parisons to the silo 2b.

Figure 4:
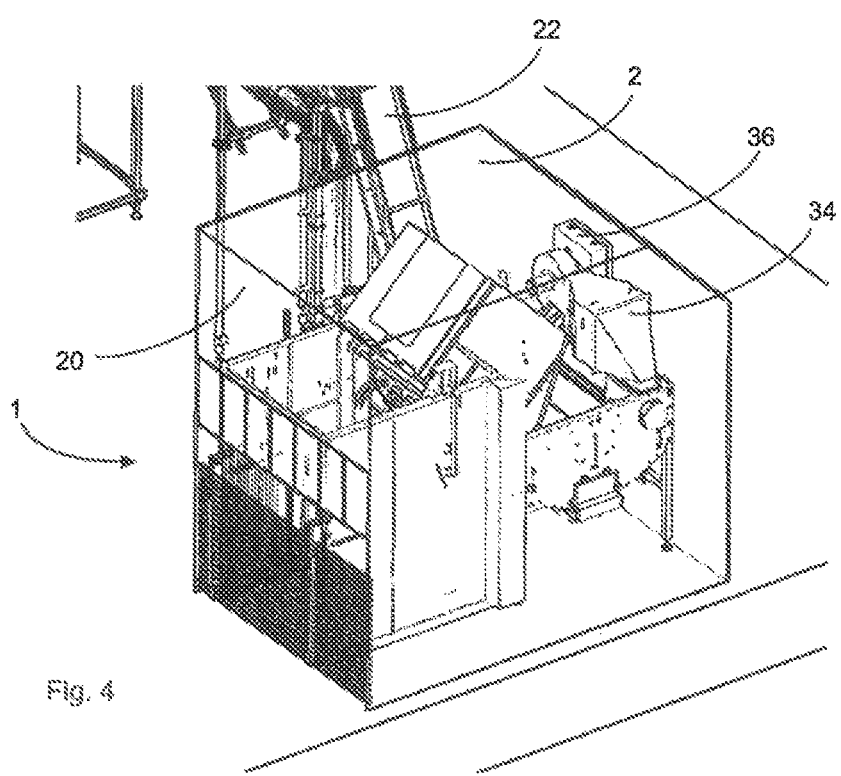
FIG. 4 shows a partial representation of a device according to the invention.

FIG. 4 shows a further detail of the device according to the invention. It can be seen here that on the rear face of the housing 20 there is a closure device which can close an opening by means of which the plastic parisons can be fed to the housing 20. In this case this closure device can nevertheless leave openings, so that in this way an air stream from the fan 34 to these openings is generated.

Figure 5:
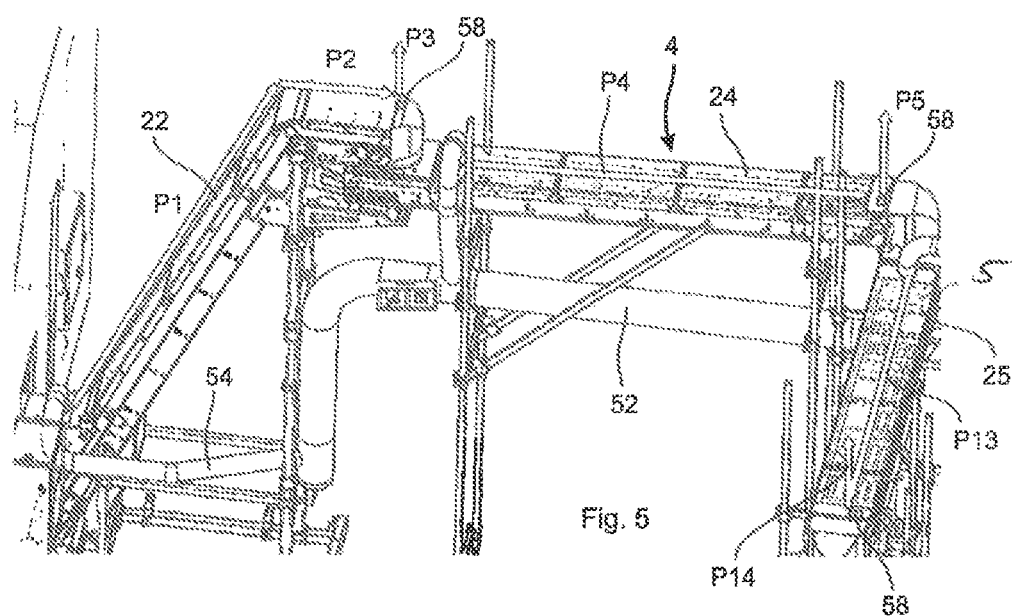
FIG. 5 shows a detail of the device shown in FIG. 4.

FIG. 5 shows a detail of the device shown in FIG. 1. In this connection in particular again the transport device 4 can be seen, which is surrounded by the housing device 24. The reference 52 designates a supply line which serves to supply the system with air. A plurality of branch lines 54 branch off from this supply line 52 and open into specific regions of the devices, such as for example into the housing 22 or also the housing 24. The arrows P1, P2 and P3 show the course of the flow inside the respective housing. The air flows here exit again through openings 58, so that the flow shown by the arrows P1, P2 and P3 is generated overall here.

Likewise the flows P4 and P5 are generated inside the housing 24. Further flows P13, P14 are generated in a housing 25. Here too an opening 58 is again provided, by means of which the air can exit from the housing 25.

The applicant reserves the right to claim all the features disclosed in the application documents as essential to the invention in so far as they are individually or in combination novel over the prior art. Furthermore it is pointed out that features which may be advantageous per se have also been described in the individual drawings. The person skilled in the art recognises immediately that a specific feature described in a drawing may also be advantageous without the incorporation of further features from this drawing. Furthermore the person skilled in the art recognises that advantages may also result from a combination of several features shown in individual drawings or different drawings.

LIST OF REFERENCES 1 device
2 storage device
2a tipper
2b silo
3 transport device
4 transport device
5 transport device
6 transport device
7 transport device
8 transport device
20 enclosure or housing
22 housing device
24 housing device
25 housing
26 housing device
28 housing device
34 ventilator device
36 fitter unit
52 supply line
52 pipe system
54 branch lines
54 pipe system
58 openings
P1-P14 air stream

The invention claimed is:

1. A device for handling plastic parisons with a storage device which serves for storing a plurality of plastic parisons and with at least one transport device which transports the plastic parisons along a predetermined transport path from the storage device to a processing device, wherein at least one portion of the storage device and of the transport path is enclosed by a housing device and an application device is provided which is configured to apply a flowable medium to an interior of the housing device, wherein the machine has a sorting device along the transport path configured for sorting the plastic parisons; and wherein the sorting device has two rotatable rollers which are spaced apart from one another and between which the plastic parisons can be transported, wherein the application device has a ventilator device configured for generating a positive pressure air stream, wherein the ventilator device is arranged inside a housing device which at least partially surrounds the storage device, and wherein the application device has a supply line which is configured for bringing said positive pressure gas stream generated by a ventilator device to a plurality of positions along the transport path of the plastic parisons.

2. The device according to claim 1, wherein the entire storage device and/or the entire transport path is enclosed by one or more housing devices.

3. The device according to claim 1, wherein the machine has a filter device configured for filtering the gaseous medium to be fed to the interior of the housing device.

4. A method for handling plastic parisons, wherein a plurality of plastic parisons are stored in a storage device and these plastic parisons are transported by at least one transport device along a predetermined transport path from the storage device to a processing device, wherein at least one portion of the storage device and of the transport path is enclosed by a housing device and an application device is provided which applies a flowable medium to an interior of the housing device, wherein the machine has a sorting device along the transport path configured for sorting the plastic parisons; and wherein the sorting device has two rotatable rollers which are spaced apart from one another and between which the plastic parisons can be transported, wherein the application device has a ventilator device configured for generating a positive pressure air stream, wherein the ventilator device is arranged inside a housing device which at least partially surrounds the storage device, and wherein the application device has a supply line which is configured for bringing said positive pressure gas stream generated by a ventilator device to a plurality of positions along the transport path of the plastic parisons.

5. The method according to claim 4, wherein a positive pressure of the gaseous medium is generated in the interior of this housing device at least in some portions and/or at least intermittently.

6. The device according to claim 1, wherein the flowable medium comprises a gas.

7. The device according to claim 6, wherein the flowable medium comprises air.

8. The device according to claim 1, wherein the entire storage device is enclosed by the housing device.

9. The method according to claim 4, wherein the flowable medium comprises a gas.

10. The method according to claim 9, wherein the flowable medium comprises air.

11. The method according to claim 4, wherein the entire storage device is enclosed by the housing device.

* * * * *